(12) United States Patent
Rivat et al.

(10) Patent No.: US 11,602,754 B2
(45) Date of Patent: Mar. 14, 2023

(54) FRAME FOR HOLDING FILTRATION ASSEMBLIES AND TESTING UNIT FOR MICROBIOLOGICAL TESTING

(71) Applicant: Merck Patent GmbH, Darmstadt (DE)

(72) Inventors: Philippe Rivat, Dorlisheim (FR); Mathieu Arrault, Dabo (FR)

(73) Assignee: Merck Patent GmbH, Darmstadt (DE)

( * ) Notice: Subject to any disclaimer, the term of this patent is extended or adjusted under 35 U.S.C. 154(b) by 484 days.

(21) Appl. No.: 16/644,576

(22) PCT Filed: Sep. 4, 2018

(86) PCT No.: PCT/EP2018/073672
§ 371 (c)(1),
(2) Date: Mar. 5, 2020

(87) PCT Pub. No.: WO2019/048400
PCT Pub. Date: Mar. 14, 2019

(65) Prior Publication Data
US 2021/0060569 A1    Mar. 4, 2021

(30) Foreign Application Priority Data
Sep. 6, 2017 (EP) .................................... 17290114

(51) Int. Cl.
*B01L 9/00* (2006.01)
*B01D 63/08* (2006.01)
(Continued)

(52) U.S. Cl.
CPC ............... *B01L 9/52* (2013.01); *B01D 63/08* (2013.01); *C12M 23/48* (2013.01); *G01N 33/48* (2013.01);
(Continued)

(58) Field of Classification Search
CPC ................. B01L 9/52; B01L 2200/021; B01L 2200/028; B01L 2200/14; B01L 2200/18;
(Continued)

(56) References Cited

U.S. PATENT DOCUMENTS

| 4,253,830 A | 3/1981 | Kazen et al. | |
| 5,308,483 A * | 5/1994 | Sklar .................... | B01D 63/087 73/863.25 |

(Continued)

FOREIGN PATENT DOCUMENTS

| CN | 203447309 U | * | 2/2014 |
| CN | 205988633 U | | 3/2017 |

(Continued)

OTHER PUBLICATIONS

English language machine translation of CN203447309U, 4 Pages, No Date.*

(Continued)

*Primary Examiner* — Pranav N Patel
(74) *Attorney, Agent, or Firm* — Millen, White, Zelano & Branigan, PC; Ryan Pool (57) ABSTRACT

The invention concerns a frame (1) for holding a plurality of filtration assemblies (100) and a testing unit (10) for microbiological testing. The frame (1) for holding the plurality of filtration assemblies (100) comprises an array of supports (5) each configured to receive and support one of the filtration assemblies (100) on a common support plane (2), and connection means (6) provided on the periphery (7) of the frame (1) and configured to releasably connect, by a form-locking engagement, a further frame (1) such that the common support planes (2) of the connected frames (1) are contiguous. Further, the testing unit (10) comprises at least one frame (1) packed in a bag (20) in pre-sterilized condition.

11 Claims, 9 Drawing Sheets

(51) Int. Cl.
  *C12M 3/00* (2006.01)
  *G01N 33/48* (2006.01)
(52) U.S. Cl.
  CPC  *B01D 2311/2688* (2013.01); *B01D 2313/025* (2013.01); *B01D 2313/13* (2013.01); *B01D 2313/20* (2013.01)
(58) Field of Classification Search
  CPC .............. B01L 9/06; B01L 2300/021; B01L 2200/023; B01L 2300/0829; B01L 9/00; B01L 2300/041; B01D 63/08; B01D 2311/2688; B01D 2313/025; B01D 2313/13; B01D 2313/20; B01D 29/085; B01D 2313/04; C12M 23/48; C12M 23/44; C12M 23/12; G01N 33/48
  See application file for complete search history.

(56) References Cited

U.S. PATENT DOCUMENTS

| | | | |
|---|---|---|---|
| 6,358,730 B1 | 3/2002 | Kane | |
| D466,219 S | 11/2002 | Wynschenk et al. | |
| 6,663,836 B1* | 12/2003 | Kalmakis | B01L 9/06 422/562 |
| 2002/0108917 A1* | 8/2002 | Maruyama | B01L 9/50 211/74 |
| 2003/0034317 A1 | 2/2003 | Lafond et al. | |
| 2005/0180895 A1* | 8/2005 | Itoh | B01L 9/06 422/400 |
| 2007/0082370 A1* | 4/2007 | Togawa | B01D 69/02 977/902 |
| 2007/0253870 A1 | 11/2007 | Weiss et al. | |
| 2016/0271612 A1 | 9/2016 | Masoumi | |

FOREIGN PATENT DOCUMENTS

| | | |
|---|---|---|
| JP | 10-174891 A | 6/1998 |
| JP | H10174891 A | 6/1998 |
| WO | 2014-197831 A1 | 12/2014 |

OTHER PUBLICATIONS

First Office Action in corresponding CN appln. 2018 80058110 dated Jun. 1, 2021 (pp. 1-4) and search report (pp. 1-3).
International Search Report dated Feb. 1, 2019 issued in corresponding PCT/EP2018/073672 application (7 pages).
English Abstract of JP H10-174891 A published Jun. 30, 1998.
Notification of Reasons for Refusal (1st Office Action) in corresponding JP 2020-513517 dated Jun. 29, 2022 (pp. 1-2).
NucleoBond Xtra Combi Rack, No. 4. Present Campaign,Takara Bio Inc., 2014 (pp. 1-2).

* cited by examiner

FRAME FOR HOLDING FILTRATION ASSEMBLIES AND TESTING UNIT FOR MICROBIOLOGICAL TESTING

TECHNICAL FIELD

The invention concerns a frame for holding a plurality of filtration assemblies and a testing unit for microbiological testing.

Filtration assemblies are known and are frequently used for microbiological testing including sterility and bio-burden testing, for example in connection with the control of manufacturing processes or final product testing in the pharmaceutical, biopharmaceutical, biotech, hospital, food and beverage industries but also for diagnostic, health care and research and in connection with other testing tasks for particles and biological elements.

During such testing a fluid to be tested is typically passed from a reservoir through a filter element, e.g. a filter membrane, which is capable of capturing microorganisms of interest. After completion of the filtration process a nutrient solution that promotes the growth of the microorganisms is brought in contact with the microorganisms captured on the filter element in order to, for example with the aid of an incubator, support the growth of the microorganisms until an analyzable size of microorganism colonies is obtained.

A filtration assembly for this process disclosed in WO 2014/197831 A1 includes a cylindrical reservoir with a conically more narrow top portion and an opening at the lower end, and a circular membrane holder holding a filter membrane. The top end of the membrane holder is removably and tightly attachable to the lower opening of the reservoir by means of a bayonet connector. The top end of the reservoir is closed except for an inlet connection for the sample fluid and a hydrophobic vent. The lower end of the circular membrane holder has a connection area designed to fit vacuum bars or pumps and culture media cartridges. After filtration the membrane holder is disconnected from the vacuum bar/pump, the reservoir is detached from the membrane holder, and the lower end of the membrane holder is attached to the culture medium cartridge to bring the filter membrane in contact with the nutrient solution and the upper end of the membrane holder is, if required, closed by a cap that allows incubating the sample under aerobic or anaerobic conditions—depending which side of the cap is plugged onto the membrane holder—and that makes the samples more easily stackable.

Problem to be Solved

The microbiological testing normally requires the simultaneous or sequential processing of batches of the same or of different sample fluids in plural filtration assemblies that form a test group. This requires that the filtration assemblies belonging to the same test group are processed as exactly as possible under the same testing conditions from storage, test set-up, filtration, transfer to media cassettes, incubation, reading/evaluation and disposal in order to make the tests of the same group comparable. Further, the tests of one test group are often carried out by several technicians working consecutively over several days or one or more technician(s) work on different test groups at the same time. This requires that the filtration assemblies belonging to a particular test group are clearly identified and handled together and this imposes significant organizing, marking and documentation work on the technicians. Further, handling errors, mixing-up of filtration assemblies between test groups or imprecision in particular during bioburden testing may require long and costly investigations.

Therefore, it is an object of the present to provide a solution to that problem that reduces the likelihood of handling errors, mixing-up of filtration assemblies between test groups or imprecision during testing procedures.

Means for Solving the Problems

To solve the problem, the present invention provides a frame, that can be also referred to as a tray, for holding a plurality of filtration assemblies and a testing unit for microbiological testing.

The present invention provides a frame for holding a plurality of filtration assemblies for microbiological testing, wherein the frame comprises an array of supports each configured to receive and support one of the filtration assemblies on a common support plane, and connection means provided on the periphery of the frame and configured to releasably connect, by a form-locking engagement, a further frame such that the common support planes of the connected frames are contiguous. The supports are preferably arranged in a regular array including rows and columns.

The frame allows that a plurality of the filtration assemblies belonging to a test group can be mechanically combined and handled together on the frame, thereby securing identical testing conditions for all filtration assemblies of the group during the complete testing procedure from storage and preparation of the assemblies, test set up, filtration, transfer to incubation, analysis and disposal.

The connection means on the frame provides the possibility of connecting or disconnecting frames in order to accommodate and handle together varying numbers of filtration assemblies of the respective group without "overhead space". Further, the arrangement of the filtration assemblies belonging to the same test group on the frame or on connected frames facilitates organisation, control, identification and documentation of the assemblies and the correctness and consistency of the association of the filtration assemblies in a particular test group can be more intuitively and easily recognized and errors can be avoided quickly.

The arrangement of the supports of one or more (connected) frames in a common plane increases the mechanical stability as compared to a simple stack of individual filtration assemblies. The rows and columns of the array of the supports are continued over several frames where several frames are connected to each other.

Preferably, the connection means comprises mating engagement features configured so that the adjacent frames can be connected to and disconnected from each other by a manual operation.

This provides the advantage that a plurality of frames can be easily and without further tools or equipment connected to each other to accommodate a larger group of filtration assemblies or can be split into sub-groups of filtration assemblies.

Preferably, the supports respectively include a securing mechanism configured to releasably fix the filtration assembly when placed on the support.

Accordingly, the filtration assembles are securely held on the frame and are prevented from falling off from the frame even when a technician handles the frame(s), for example during transfer to incubation or analysis.

Preferably, the securing mechanism is configured to resiliently engage with an outer circumference of the filtration assembly, preferably by a snap-fit.

Accordingly, the filtration assemblies can be inserted and attached to the support in a simple process and removal requires an active process to overcome the bias-holding force imparted by the resiliency, thereby avoiding handling errors and unintentional removal of assemblies from the frame.

Preferably, the frame comprises a spacer configured to raise the support plane above a work surface and to define a space on the underside of the frame.

Preferably, each support is provided with an opening extending through the frame and arranged so as to expose at least a part of a bottom portion of the filtration assembly to the space defined on the underside of the frame.

The spacer improves the stability of the frame and avoids a direct contact between the lower parts of the filtration assemblies and the work surface. Further, the space reduces the risk of contamination and, in combination with the openings of the supports, secures substantially unimpeded flow of air through the space on the underside of the frame to the filtration assemblies in order to provide comparable and homogenous incubation conditions.

Preferably, the support includes a cover element suspended in the opening and configured to cover and/or seal a discharge port of the filtration assembly when the filtration assembly is placed on the support.

The cover element provides specific protection for filtration assemblies that include a drain member with a discharge port protruding from the bottom side and avoids contamination of the membrane through the opening in the discharge port or damage of the discharge port and prevents any fluid from dripping from the discharge port in case the filtration assemblies are transferred to the frame after filtration.

Preferably, the cover element is suspended in the opening by one or more web(s) connecting the cover element to the frame so that at least a portion of the opening remains uncovered and exposed to the space on the underside of the frame.

Since the cover element does not completely block the opening of the support the air can still reach the underside of the filtration assembly, thereby securing equal incubation conditions and an even temperature distribution among the assemblies on the frame.

Preferably, the spacer is formed as a peripheral skirt of the frame and the skirt includes one or more opening(s) that provide(s) communication between the outer periphery of the frame and the space defined on the underside of the frame to allow an air flow to the openings of the supports. The air flow and the open space specifically assure homogenous growth conditions in each of the filtration assemblies (or elements thereof like incubation cassettes) by assuring an homogenous temperature distribution and a good gradient of temperature during incubation.

The peripheral skirt provides improved stability to the frame and the openings provide gaps in the skirt that allow air to pass into and through the space below the frame and visual inspection of the underside of the frame.

Preferably, the spacer is formed so that two or more of the frames vertically stacked upon each other are nested inside each other.

The nesting reduces the vertical height of a stack of empty frames and makes the stack more compact for storage.

Preferably, each support comprises a recess for receiving a skirt of the filtration assembly to be placed on the support.

The recess provides that the filtration assemblies can be more stably held on the frame.

Preferably, the frame further comprises coding means associated to each support in the array.

The coding means provides a possibility of adding identification information, for example a colour code, concerning the filtration assemblies loaded on the frame, i.e. allowing a distinction of membrane material, sample batch, technician that has performed the testing etc. The invention also provides a testing unit for microbiological testing, comprising at least one frame for holding filtration assemblies according to the invention packed in a bag in a pre-sterilized condition. Preferably, a plurality of filtration assemblies are supported on the supports of the frame(s) and are also packed in the bag in a pre-sterilized condition.

The packing of one or more pre-sterilized frames in a bag provides the advantage that the frames are ready to use and do not require sterilisation.

Where several frames are provided in the bag in a connected state, a technician can easily split or separate the frames at the connection means into sub-groups while the frames are still in the bag where a smaller amount of supports is required for a test group and can keep the rest of the frames in the sterile packing.

BRIEF DESCRIPTION OF THE DRAWINGS

Preferred embodiments of the frame for holding filtration assemblies and of the testing unit according to the present invention will be described by reference to the attached drawing, in which.

DETAILED DESCRIPTION OF THE EMBODIMENTS

Figure 1:
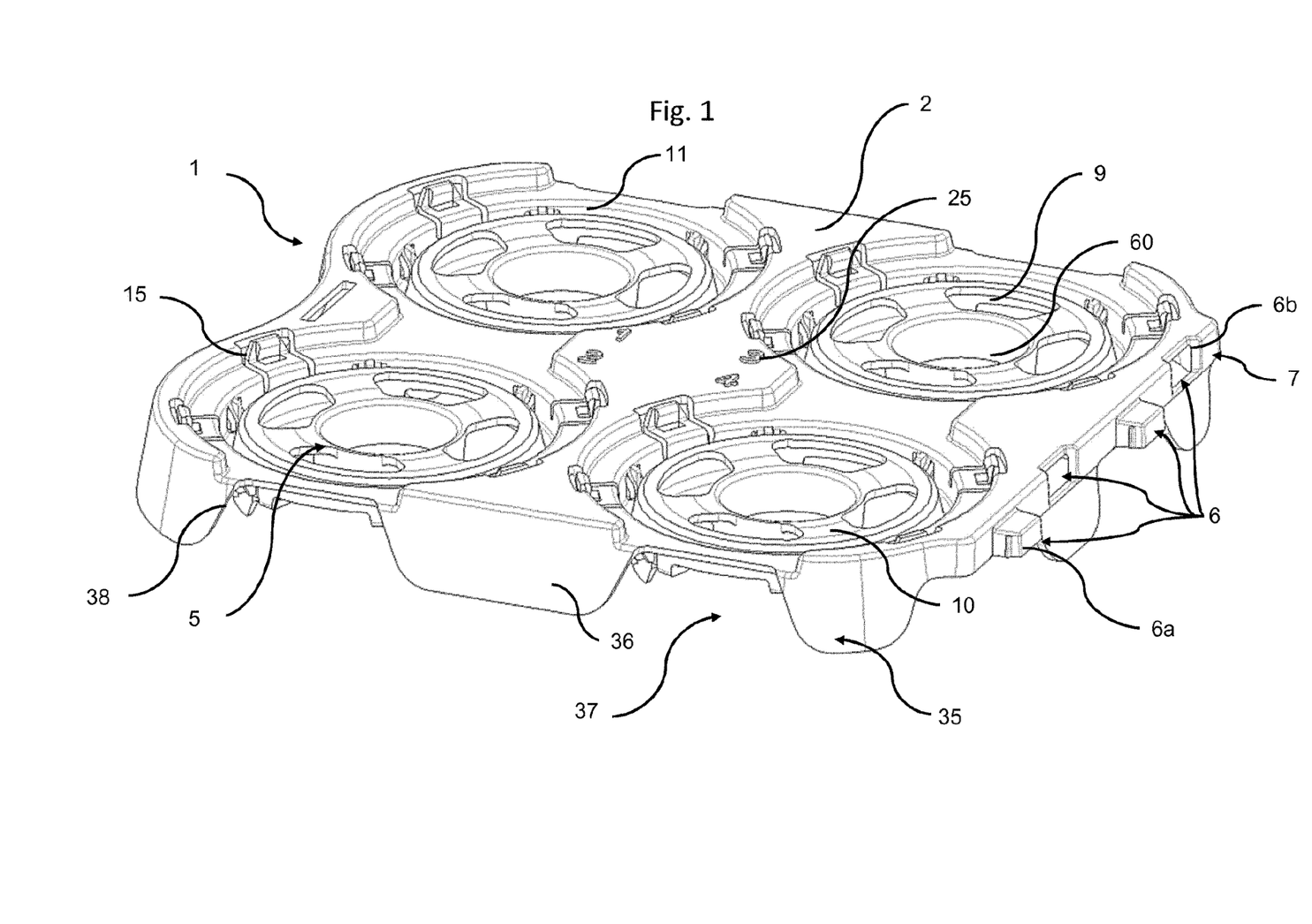
FIG. 1 is a perspective view showing a frame according to an embodiment of the present invention from a top.

A frame 1 or tray for holding a plurality of filtration assemblies 100 for microbiological testing according to an embodiment of the present invention is shown in FIG. 1. The frame 1 comprises an array of supports 5 in rows and columns, wherein each support 5 is configured to receive and support, i.e. hold one of the filtration assemblies 100 on a common support plane 2, and a connection means 6 provided on one side of the periphery of the frame 1. The connection means 6 is configured to releasably connect a further frame 1 of the same type by a form-locking engagement such that the support planes 2 of the connected frames 1 are contiguous, i.e. are aligned with each other.

The frame 1 may be made of a thermoplastic resin and may include not only four supports in two rows and two columns but may have any practical number of supports as long as at least two supports are provided. The frame 1 in this case has an outer periphery 7 in the form of a skirt 36 that is substantially shaped like a rectangle with rounded corners. The skirt 36 is integrally formed to extend substantially perpendicular to connections defining the support plane 2.

Figure 2:
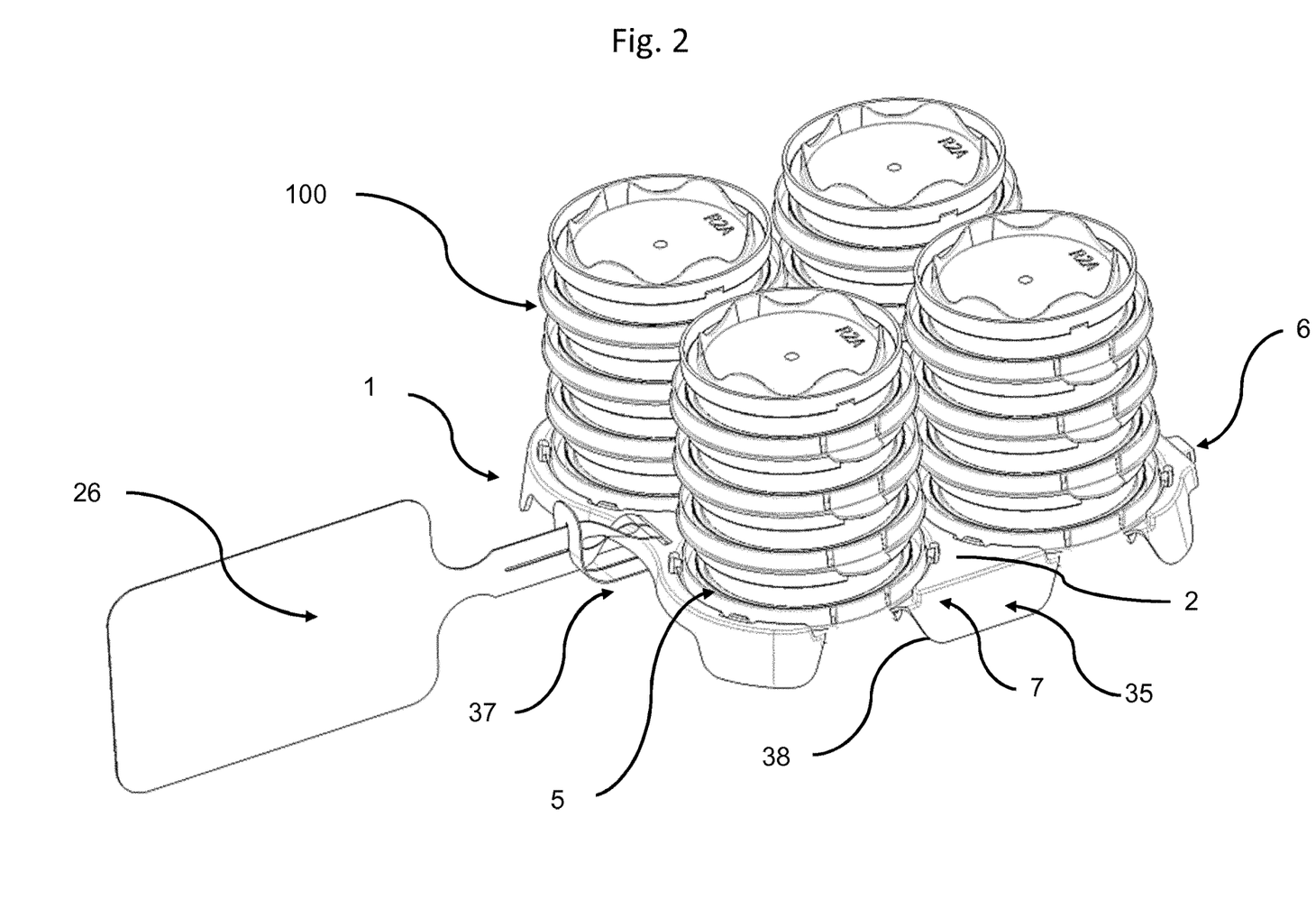
FIG. 2 is a perspective view showing the frame according to the embodiment of the present invention with a plurality of media cassettes placed on supports of the frame.

Each support 5 is formed so as to be able to receive a filtration assembly 100 and has one or more recesses to accommodate protrusions on the bottom portion of the respective assembly 100, including for example a recess 11 into which a skirt portion of the assembly 100 can be inserted and at least partly accommodated. Each of the filtration assemblies 100 when placed on the support 5 is supported on the common support plane 2 and is prevented from lateral movement. In addition, as shown in FIG. 2, the supports 5 may be formed to receive the various elements of the filtration assemblies 100 including reservoirs, membrane holders, media cassettes or the like.

The connection means 6 is formed to establish a releasable mechanical connection between at least two adjacent frames 1 that is rigid enough to allow the handling of the connected frames 1 as a unit. In the embodiment the connection means 6 are provided on only one lateral side of the periphery 7 of the frame 1, thus limiting the number of frames 1 that can be connected to two. If connection means 6 are provided on the opposite lateral sides of each frame 1 a plurality of frames 1 can be connected in a row and if they are provided on each of the four lateral sides of the periphery 7, frames 1 can be connected to each side to form a larger array. The connection means 6 is configured such that the frames 1 can be easily connected or disconnected by hand but remain connected during the normal handling of the frames 1 in the connected state. For example, the connecting means 6 can be designed so that the frames 1 may be connected or disconnected by moving the frames 1 relative to each other in a defined manner such as a rotation (see FIGS. 8A and 8B) or a lateral parallel movement.

Figure 3:
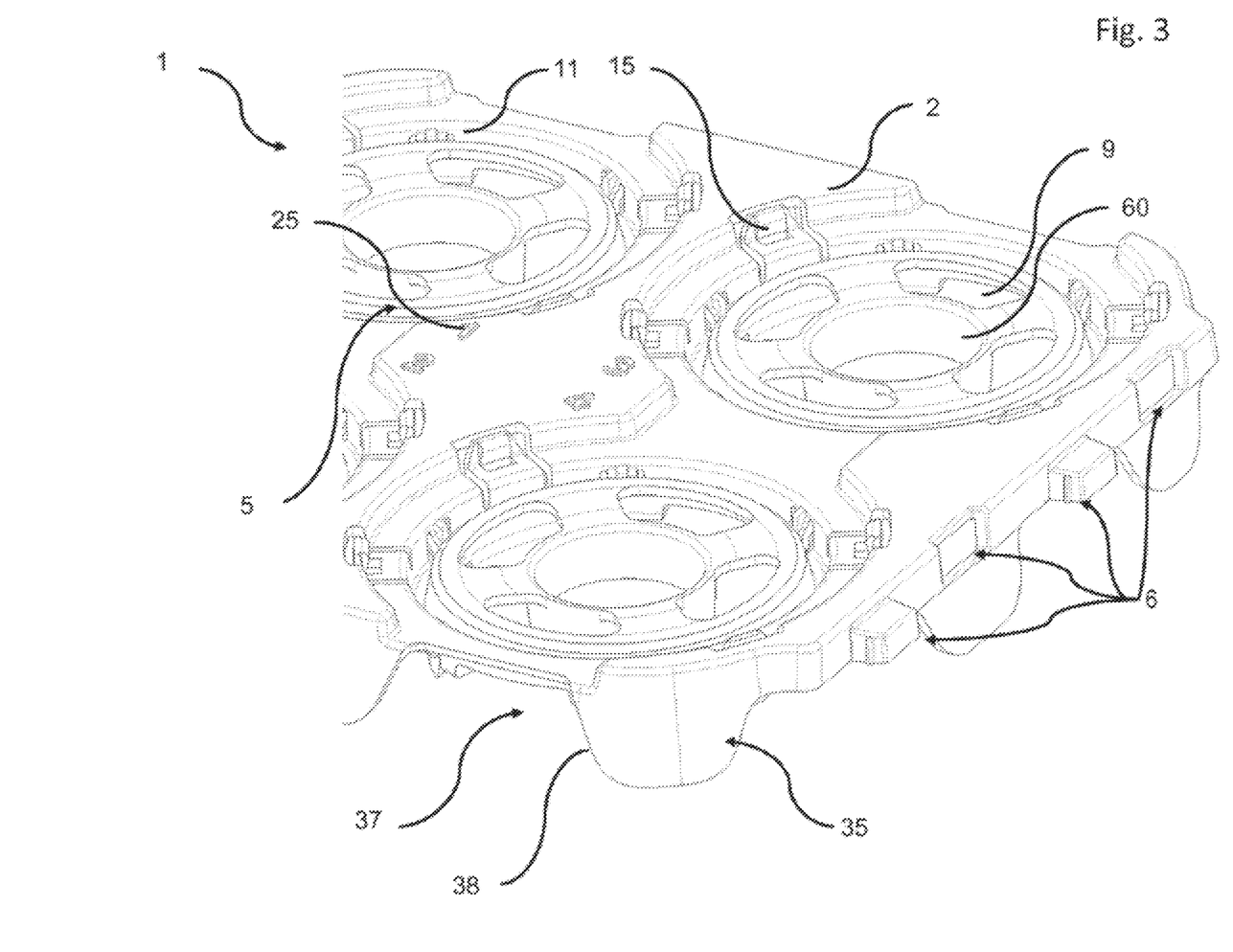
FIG. 3 is a perspective enlarged view of a portion of the frame of FIG. 1.

In the embodiment the connection means 6 includes a male holding tab 6a and a mating female slot 6b formed to receive the holding tab 6a. As shown in FIG. 3 two male holding tabs 6a and two female slots 6b are formed on one lateral side of the frame 1 adjacent to each other in an alternating manner so that two identical frames, if turned by 180 degrees, can be connected by engaging male tabs with opposed female slots. As mentioned above additional tabs and slots can be formed on opposite lateral sides or on all four lateral sides of the frame 1.

The supports 5 on the frame 1 can include a securing means 15 configured to releasably hold and secure the filtration assembly 100 when placed on the support 5. The securing means 15 may provide a retention of the filtration assembly 100 by a snap-fit, by a press fit, by a bayonet-type locking engagement or by adhesive force.

In the embodiment the securing means 15 is in the form of plural resilient latches that can engage with a rim or edge or recess on an outer circumference or periphery of the filtration assembly 100, preferably by a snap-fit, when the filtration assembly 100 is placed on and pressed downward into the support 5. The latches may be formed to apply a biasing force in the engagement direction that must be overcome by manual operation to release the filtration assembly 100 from the support 5.

In the embodiment, the support 5 is provided with four securing means 15 in the form of latches distributed about the circumference of the support. A smaller and larger number of securing means 15 may be provided on the support 5.

Each support 5 is provided with an opening 9 that extends through the frame 1 to provide a communication between the top and bottom sides and is arranged so as to expose at least a part of a bottom portion of the filtration assembly 100 to the space 37 defined on the underside of the frame 1.

Figure 5:
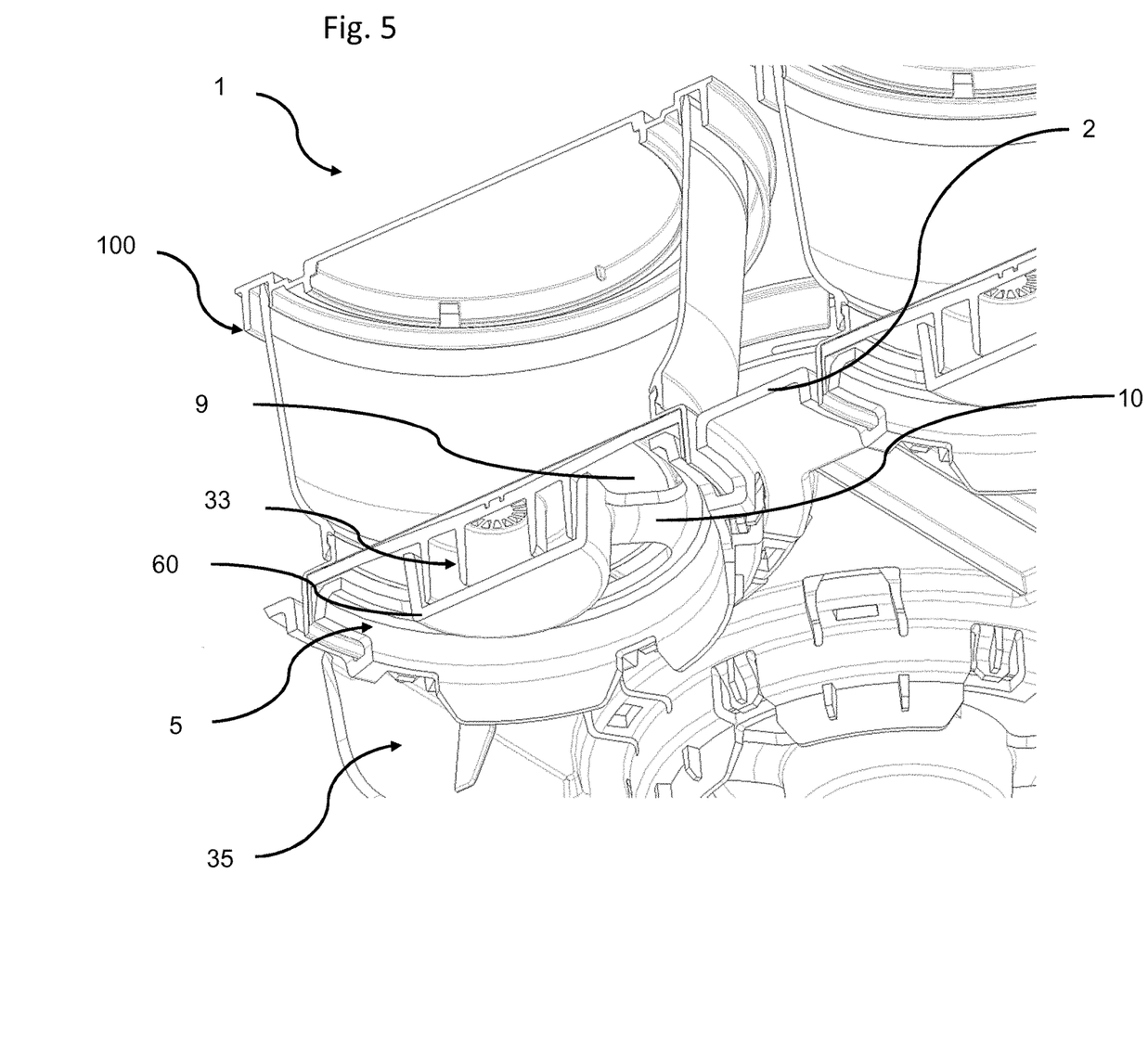
FIG. 5 is a perspective sectional view showing a support when a filtration assembly is placed on the support.
Figure 6:
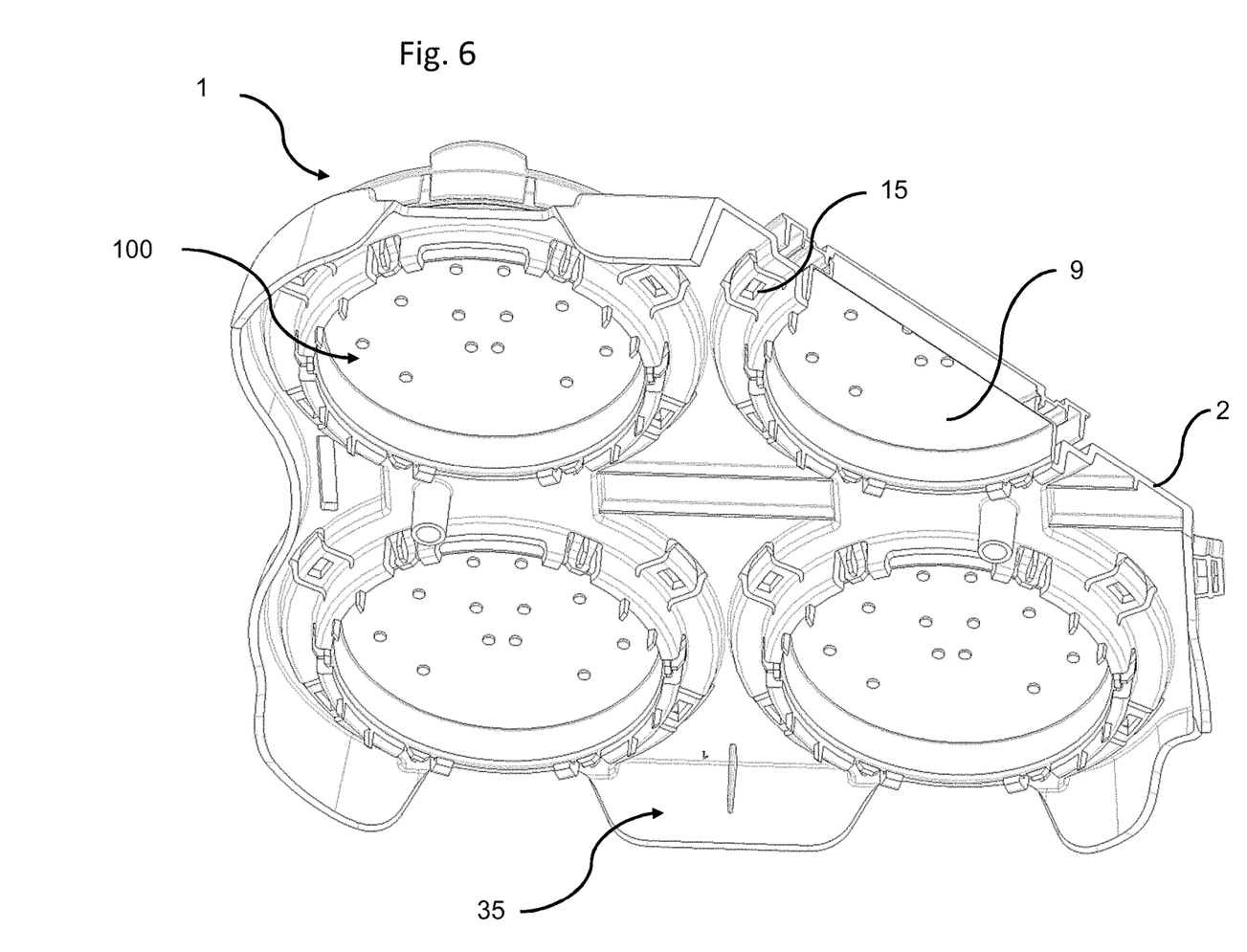
FIG. 6 is a perspective view from below showing an embodiment of a frame having an opening in a support and a media cassette placed on the support.

The support 5 includes a cover element 60 that is suspended in the opening 9 and that is configured to cover and/or seal a discharge port 33 of the filtration assembly when the filtration assembly 100 is placed on the support 5. The cover element 60 is shaped like a cup into which the protruding discharge port 33 can be inserted as shown in FIG. 5. The cup of the cover element 60 is suspended in the opening 9 by one or more web(s) 10, four in the embodiment, evenly spaced about the opening 9 and connecting the cup of the cover element 60 to the frame 1 at the periphery of the opening 9 so that at least a portion of the opening 9 remains uncovered and exposed to the space 37 on the underside of the frame 1.

If needed, the cover element 60 may include a seal to fluid-tightly close an opening of the discharge port 33 when the filtration assembly 100 is placed on the support 5.

Further, the cover element 60 may be removable from the opening 9 such that the opening 9 is fully open. For example, the web(s) 10 may have a predetermined breaking or cutting point or a weakened zone that allows severing of the web(s) 10 to remove the cover element 60.

The opening 9 can serve as an analysing window for visual inspection of filtration assemblies 100 or of elements thereof from below or from the side and it may be provided with a transparent disk, for example made of glass or resin.

The frame 1 comprises a spacer 35 in the form of the skirt 36 on the outer periphery 7 of the frame 1 which raises the support plane 2 above a work surface and defines the space 37 on the underside of the frame 1, i.e. between the frame 1 and the work surface. The work surface may be for example a table surface on which the frame 1 is placed. The space 37 between the frame 1 and the work surface is dimensioned to avoid a contact of the bottom of the filtration assembly 100 with the work surface and to allow air to pass through the underside of the frame 1 towards the bottom portions of the filtration assemblies 100 exposed at the openings of the supports. The spacers 35 may be alternatively in the form of a number of posts of various shapes distributed about the frame 1.

The spacer 35 in the embodiment in the form of the skirt 36 includes one or more opening(s) 38 that provide(s) communication between the outer periphery of the frame 1 and the space 37 defined on the underside of the frame 1 to allow air to flow to and from the openings 9 of the supports 5. The openings 38 may be in the form of gaps in the skirt as shown or may be realized by through holes provided in the skirt of the frame 1 or can be realized by a spacing between posts forming the spacers.

Figure 4:
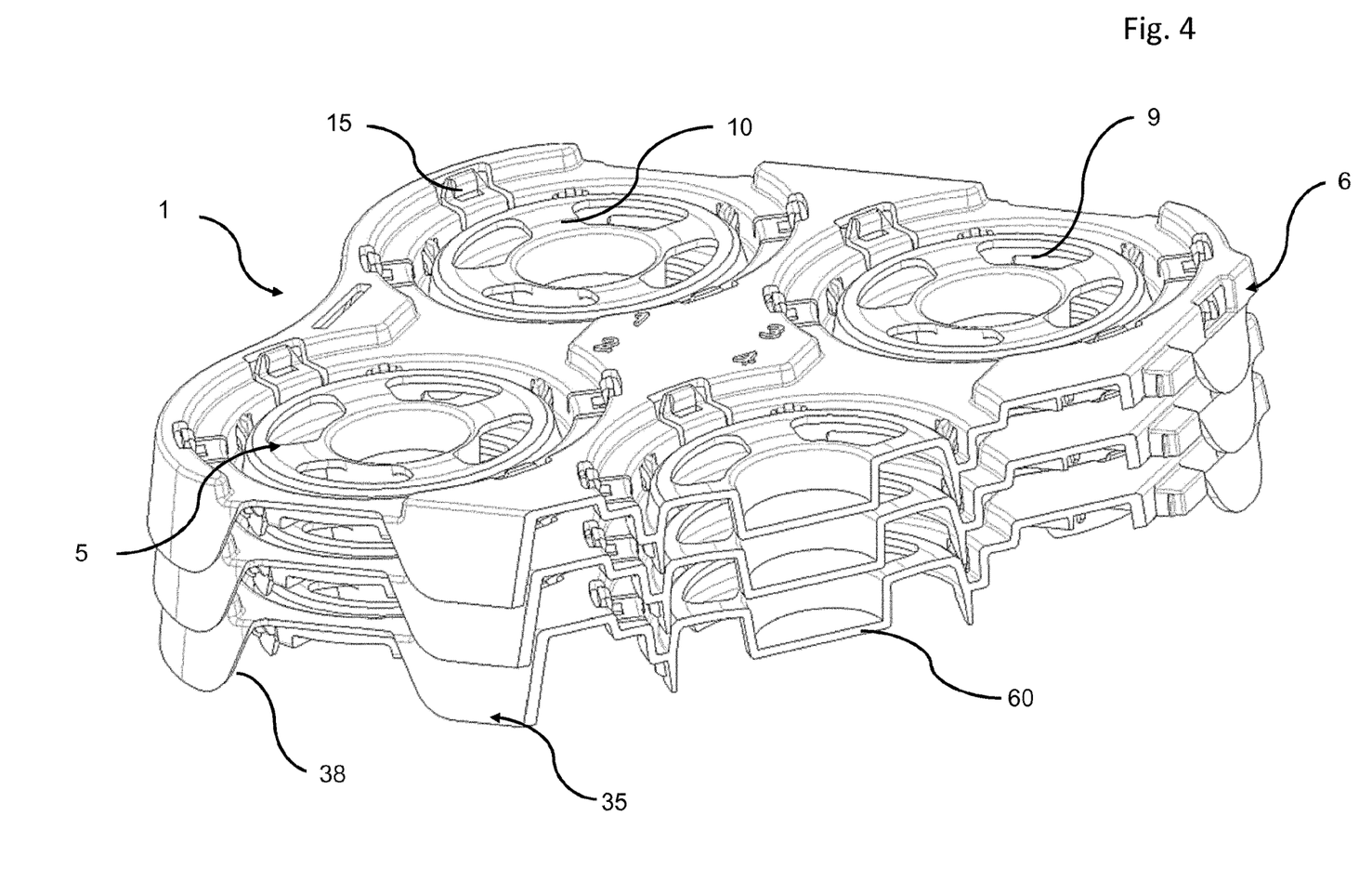
FIG. 4 is a perspective sectional view showing a plurality of stacked frames nested inside each other.

The spacer 35 and, if provided, other protruding portions on the frames 1 like the cover elements 60 or recesses 11 are formed so that two or more of the frames 1 having the same configuration can be vertically stacked upon each other and are nested inside each other so that the stack has a reduced height as compared to the sum of the height of the individual frames (see FIG. 4). For example, the skirt forming the spacer in the embodiment can be slightly inclined so that the skirt of a stacked upper frame can at least partly slide along the skirt of the lower frame in the stack as shown in FIG. 4.

The frame 1 may further comprise a coding means 25 associated to each support 5 in the array and/or the frame as such and configured to provide information in relation to the support and/or frame. The coding means can be in the form of machine readable codes like a bar code, a tag or section allowing direct writing or fixing of stickers (see FIG. 2 for an example of a tag 26 for labeling attached to an opening of the frame), or may be in the form of a coloring that is either integral with the frame or supports or can be adapted by attaching, for example, rings or tabs of different color, or a combination thereof. The coding means, especially coloring, allows simple, quick and intuitive association between the elements of the filtration assemblies held on the frame(s) and allows a simple identification of match or mismatch (and error in this case) if the elements of the filtration assemblies have a corresponding code attached to it. The coding means of the frame and/or of the supports allows a simple tracking of components if, for example, a plurality of frames that have been initially connected at the connection means are separated from each other during a particular process.

Figure 7:
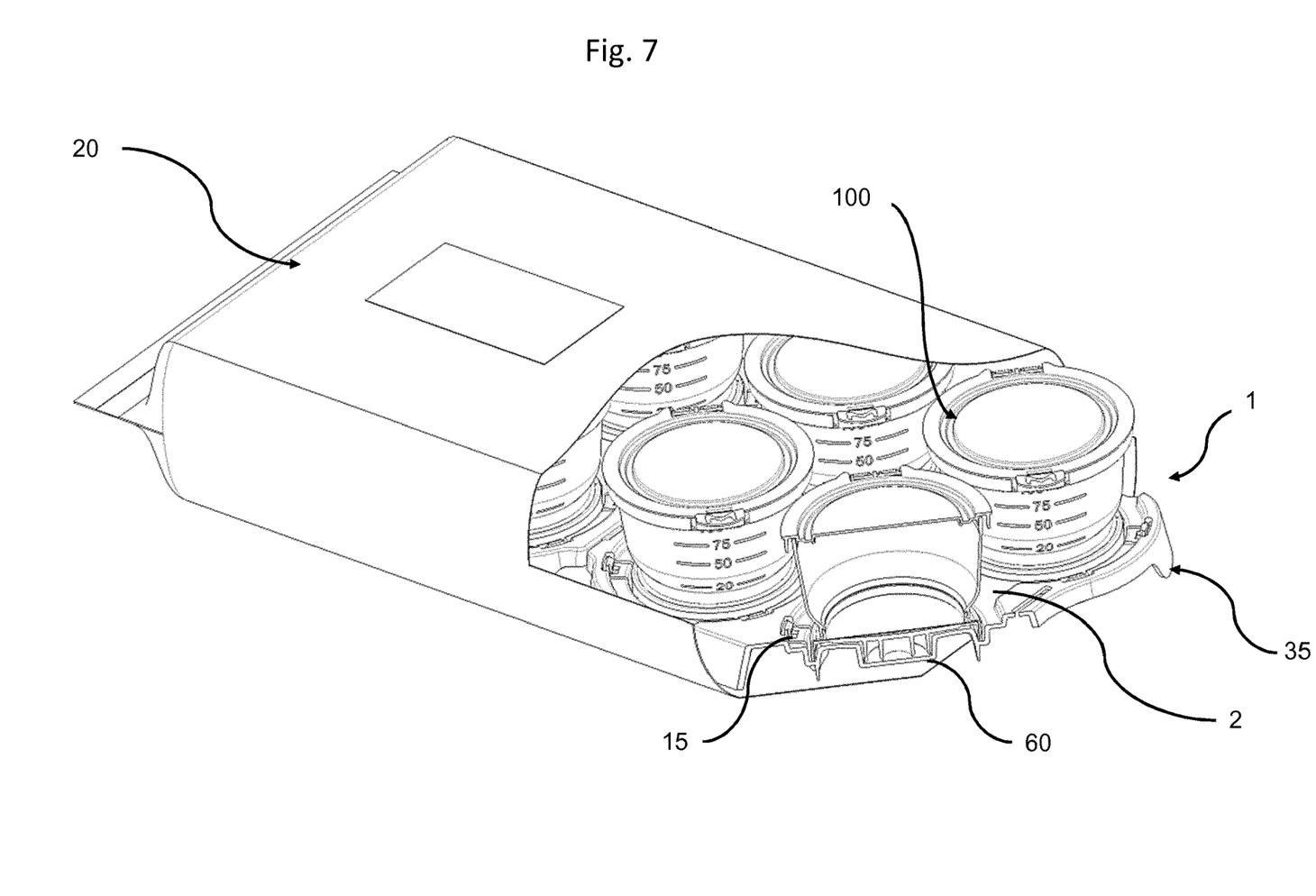
FIG. 7 is a sectional perspective view showing a packed testing unit with frames and filtration assemblies placed on the frames.
Figure 8A:
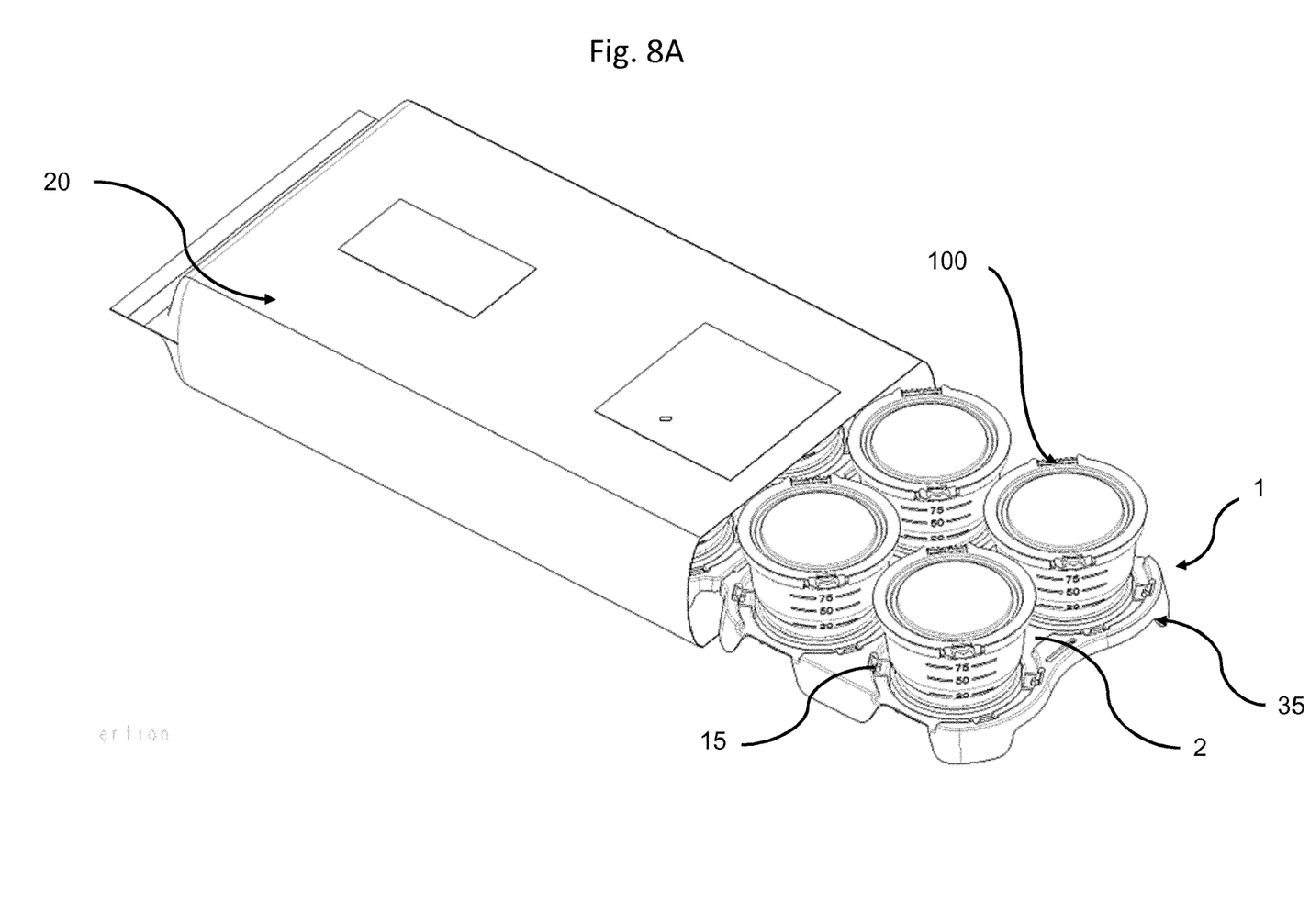
FIG. 8A and FIG. 8B are perspective views showing the unpacking of frames with filtration assemblies from the filtration unit of FIG. 7.
Figure 8B:
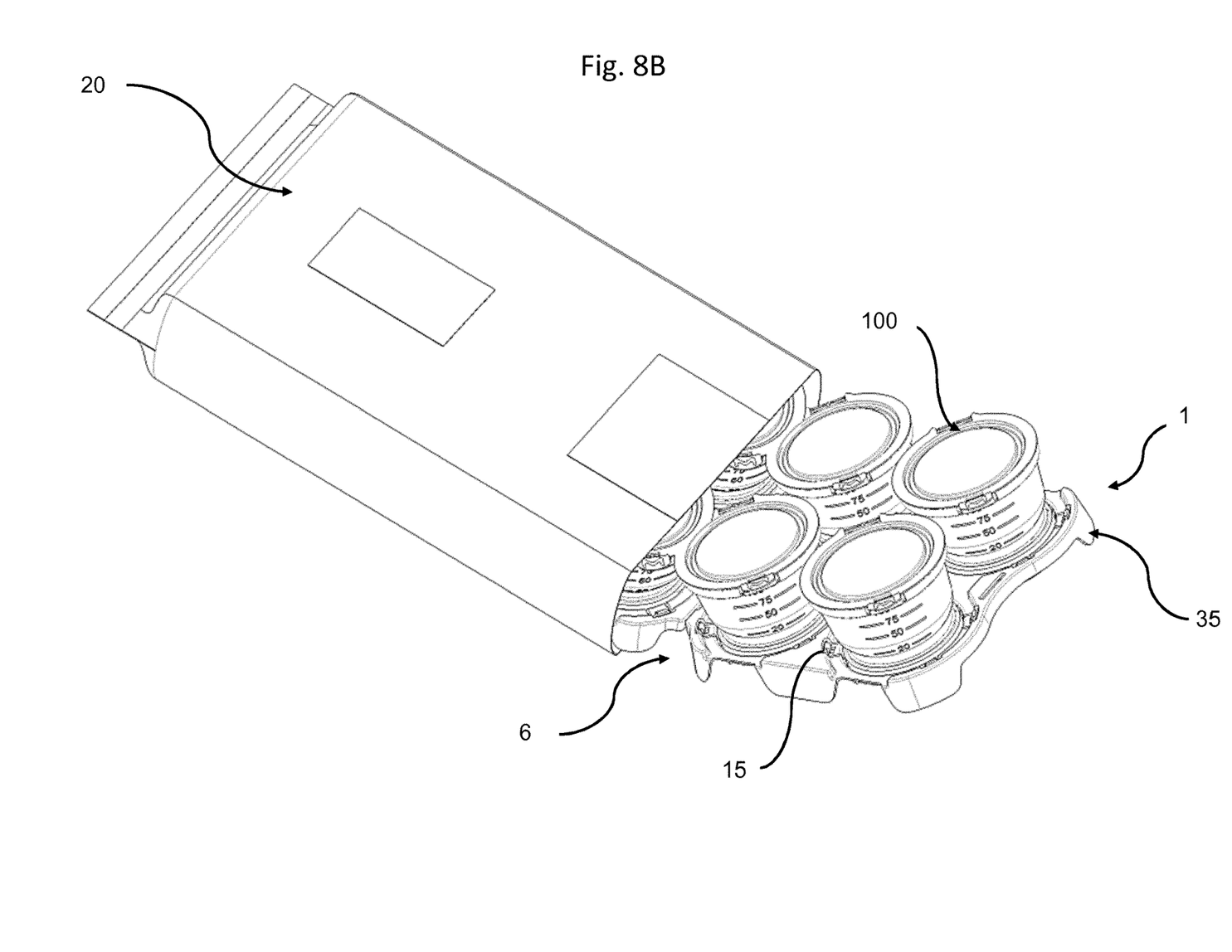

A testing unit 10 for microbiological testing is shown in FIG. 7 and comprises one or more frame(s) 1 of the invention, preferably in connected state, for holding filtration assemblies 100 packed in a bag 20 in pre-sterilized condition. The bag 20 may be made of a suitable material that is easy to sterilize inside, maintains the sterility over a required period of time, is easy to open, preferably manually and without any tool, is preferably re-closable in a sterile condition, and provides sufficient stability for transport and storing. The material may be resin, preferably Polyethylene. An opening of the bag 20 may be re-sealable by means of zipper, adhesive, clamp or the like. Where a plurality of connected frames are received in the bag as shown in FIG. 8A and FIG. 8B a user may withdraw a part of the frames from the opening and disconnect the desired part at the connecting means, here by bending, and put back the unused frames into the sterile bag and re-seal the opening. If the bag is flexible and transparent and suitable sized the disconnection could be made while the frames are still completely in the bag.

The testing unit of the invention can already include a plurality of filtration assemblies 100 supported on the supports 5 of the frame(s) 1 packed in the bag 20 in pre-sterilized condition as shown in FIGS. 7, 8A and 8B. The filtration units as shown here include as its elements a membrane support, a drain member attached to the underside of the membrane support (see FIG. 5), a reservoir attached to the upper side of the membrane support, and a lid attached to a top opening of the reservoir. In addition, a mating incubation or media cassette may be included as well (not shown) and arranged, for example, on top the lid. The elements of the filtration assemblies in a packaged unit and the frame can be provided with consistent color coding to facilitate the identification of different membrane types and/or volumes and/or incubation media.

In practice, the filtration assemblies 100 of the filtration unit are delivered placed on the supports 5 of the frame(s). In this state an opening of a discharge port of the drain member of the filtration assemblies 100 is covered and/or sealed by the cover element of the respective support (if provided). When the filtration assemblies 100 are used for filtrating, they are individually removed from the supports 5. After filtration, when the drain member is no longer needed and removed from the membrane support of the filtration assembly, the cover elements 60 and the webs holding it can be removed from the opening of the supports to increase the size thereof if needed. Then, the membrane support of the filtration assembly can be separated from the reservoir, the membrane support can be placed on top of the media cassette of the filtration assembly, and the so formed incubation unit can be placed on the support of the frame again. The lid can be removed from the reservoir and re-attached to the top of the membrane support in this incubation unit. The media cassette can be visually inspected from below the support plane through the opening in the support.

Further, the filtration assemblies 100 and its elements like the media cassettes may be configured so that a plurality of these elements can be stacked on top of each other on the supports 5 and the frames are also configured that they can in return be stacked on top of the lids of the filtration assemblies so that plural filtration units with frames with filtration assemblies placed on the supports can be stacked on top of each other.

REFERENCE SIGNS 1 frame/tray
2 support plane
100 filtration assembly
5 support
6 connection means
6a male holding tap
6b female slot
7 periphery of frame
9 opening
10 web
11 recess
15 securing mechanism
20 bag
25 coding means
26 tag for labelling
33 discharge port
35 spacer
36 skirt
37 space
38 opening
60 cover element

The invention claimed is:

1. A frame (1) for holding a plurality of filtration assemblies (100) for microbiological testing, wherein the frame (1) comprises:
an array of supports (5) wherein each array of supports are positioned and suitable to receive and support one of the filtration assemblies (100) on a common support plane (2),
a connector (6) provided on a periphery (7) of the frame (1) and configured to releasably connect, by a form-locking engagement, a further frame (1) such that common support planes (2) of the connected frames (1) are contiguous, and
a plurality of filtration assemblies (100), wherein filtration assemblies (100) comprise
a membrane support,
a drain member attached to the underside of the membrane support,
a reservoir attached to the upper side of the membrane support, and
a lid attached to a top opening of the reservoir; and
a spacer (35) positioned and suitable to raise the support plane (2) above a work surface and to define a space (37) on the underside of the frame (1),
wherein the spacer (35) is formed as a peripheral skirt (36) of the frame (1) and the skirt (36) includes one or more opening(s) (38) that provide(s) communication between the outer periphery of the frame (1) and the space (37) defined on the underside of the frame (1) to allow an air flow to the openings of the supports (5).

2. The frame (1) according to claim 1, wherein the connector (6) comprises mating engagement features configured so that adjacent frames (1) can be connected to and disconnected from each other by manual operation.

3. The frame (1) according to claim 1, wherein the supports (5) respectively include a securing mechanism (15) wherein said securing mechanism is positioned and suitable to releasably fix a filtration assembly (100) when placed on the support (5).

4. The frame (1) according to claim 3, wherein the securing mechanism (15) wherein said securing mechanism is positioned and suitable to engage with an outer circumference of the filtration assembly (100).

5. The frame (1) according to claim 1, wherein each of the supports (5) is provided with an opening (9) extending through the frame and arranged so as to expose at least a part of a bottom portion of the filtration assembly (100) to the space (37) defined on the underside of the frame (1).

6. The frame (1) according to claim 5, wherein the support (5) includes a cover element (60) suspended in the opening (9) and wherein said cover element is positioned and suitable to cover and/or seal a discharge port (33) of the filtration assembly (100) when the filtration assembly (100) is placed on the support (5).

7. The frame (1) according to claim 6, wherein the cover element (60) is suspended in the opening (9) by one or more web(s) (10) connecting the cover element (60) to the frame so that at least a portion of the opening (9) remains uncovered and exposed to the space (37) on the underside of the frame (1).

8. The frame (1) according to claim 1, wherein the spacer (35) is formed so that two of the frames (1) are vertically stacked upon each other and are nested inside each other.

9. The frame (1) according to claim 1, wherein each support (5) comprises a recess (11) for receiving a skirt of the spacer (35) to be placed on the support (5).

10. The frame (1) according to claim 1, further comprising:
 a coder (25;26) associated to the frame (1) and/or each of the supports (5) in the array,
 wherein the coder is selected from the group consisting of machine-readable codes, a tag or section suitable for direct writing or fixing of stickers, and a coloring.

11. The frame (1) according to claim 1, wherein the supports (5) are arranged in an array including rows and columns.

* * * * *